(12) United States Patent
Roberts et al.

(10) Patent No.: US 11,826,497 B2
(45) Date of Patent: Nov. 28, 2023

(54) APPARATUS FOR DEODORIZING A SPACE AND METHOD OF USING THE APPARATUS

(71) Applicant: DEO COMPANY LLC, Palatine, IL (US)

(72) Inventors: Drake Roberts, Palatine, IL (US); Anthony Tamras, Island Lake, IL (US)

(73) Assignee: DEO COMPANY LLC, Palatine, IL (US)

( * ) Notice: Subject to any disclaimer, the term of this patent is extended or adjusted under 35 U.S.C. 154(b) by 0 days.

(21) Appl. No.: 18/128,893

(22) Filed: Mar. 30, 2023

(65) Prior Publication Data

US 2023/0233729 A1 Jul. 27, 2023

Related U.S. Application Data

(63) Continuation-in-part of application No. 17/005,689, filed on Aug. 28, 2020, which is a continuation-in-part of application No. 15/964,849, filed on Apr. 27, 2018, now abandoned.

(60) Provisional application No. 62/491,747, filed on Apr. 28, 2017.

(51) Int. Cl.
    *A62B 7/08* (2006.01)
    *A61L 9/00* (2006.01)
    *A24F 25/00* (2006.01)
    *A61L 9/12* (2006.01)
    *A61L 9/04* (2006.01)

(52) U.S. Cl.
    CPC .............. *A61L 9/12* (2013.01); *A61L 9/048* (2013.01); *A61L 2209/133* (2013.01); *A61L 2209/134* (2013.01)

(58) Field of Classification Search
    CPC . A61L 9/04; A61L 2209/133; A61L 2209/134
    USPC .............................. 422/123, 306; 239/35, 56
    See application file for complete search history.

(56) References Cited

U.S. PATENT DOCUMENTS 4,258,004 A * 3/1981 Valenzona ................ A61L 9/12
                                                239/57
5,180,107 A * 1/1993 Lindauer ................... A61L 9/12
                                                261/DIG. 65

* cited by examiner

*Primary Examiner* — Monzer R Chorbaji
(74) *Attorney, Agent, or Firm* — Wood, Phillips, Katz, Clark & Mortimer

(57) ABSTRACT

A portable deodorizing apparatus having: a housing with first and second releasably joinable parts; and a deodorant source. The first housing part has a first connector and the second housing part has a second connector. The connectors are configured to be: a) engaged so as to thereby maintain the first and second housing parts in an operative relationship as an incident of relatively moving the first and second housing parts from a starting relationship into the operative relationship; and b) disengaged as an incident of relatively moving the first and second housing parts with the first and second housing parts in the operative relationship, so as to thereby allow the first and second housing parts to be changed from the operative relationship into the starting relationship. With the first and second housing parts in the operative relationship, the deodorant source is maintained in an operative position wherein deodorant is diffused into a space within which the deodorizing apparatus is placed.

28 Claims, 11 Drawing Sheets

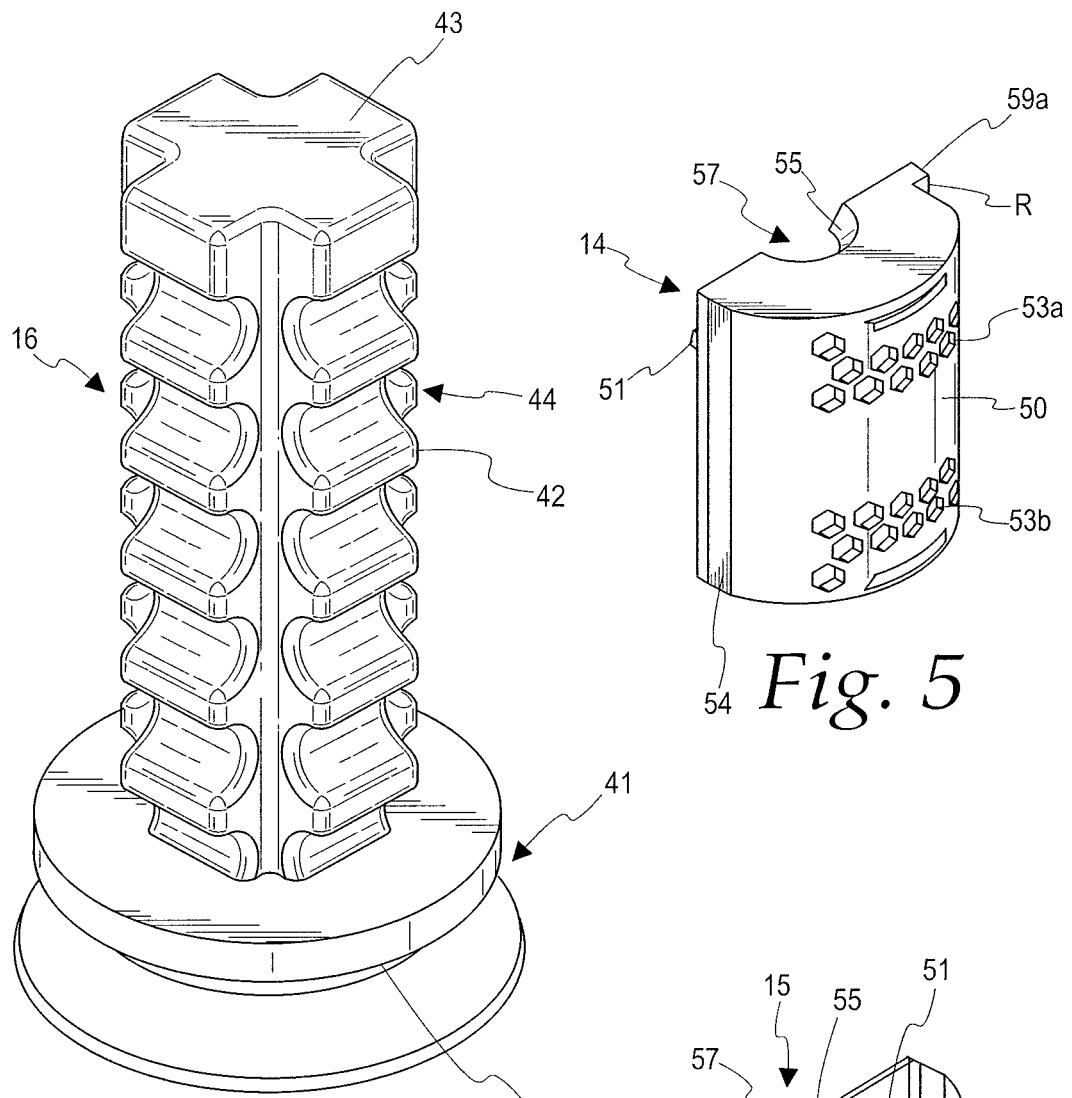
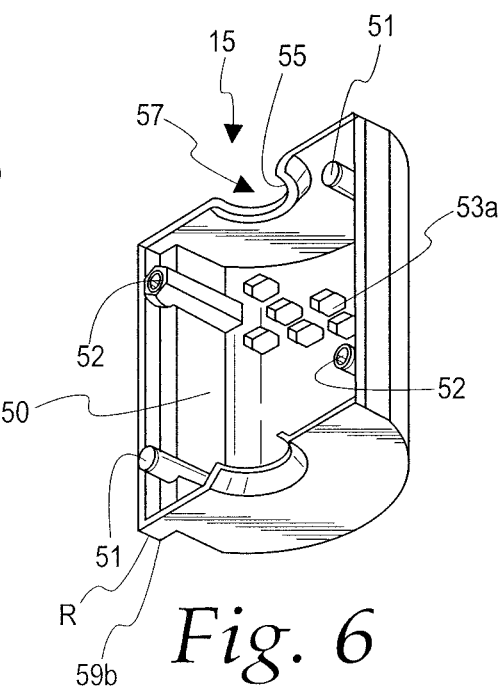

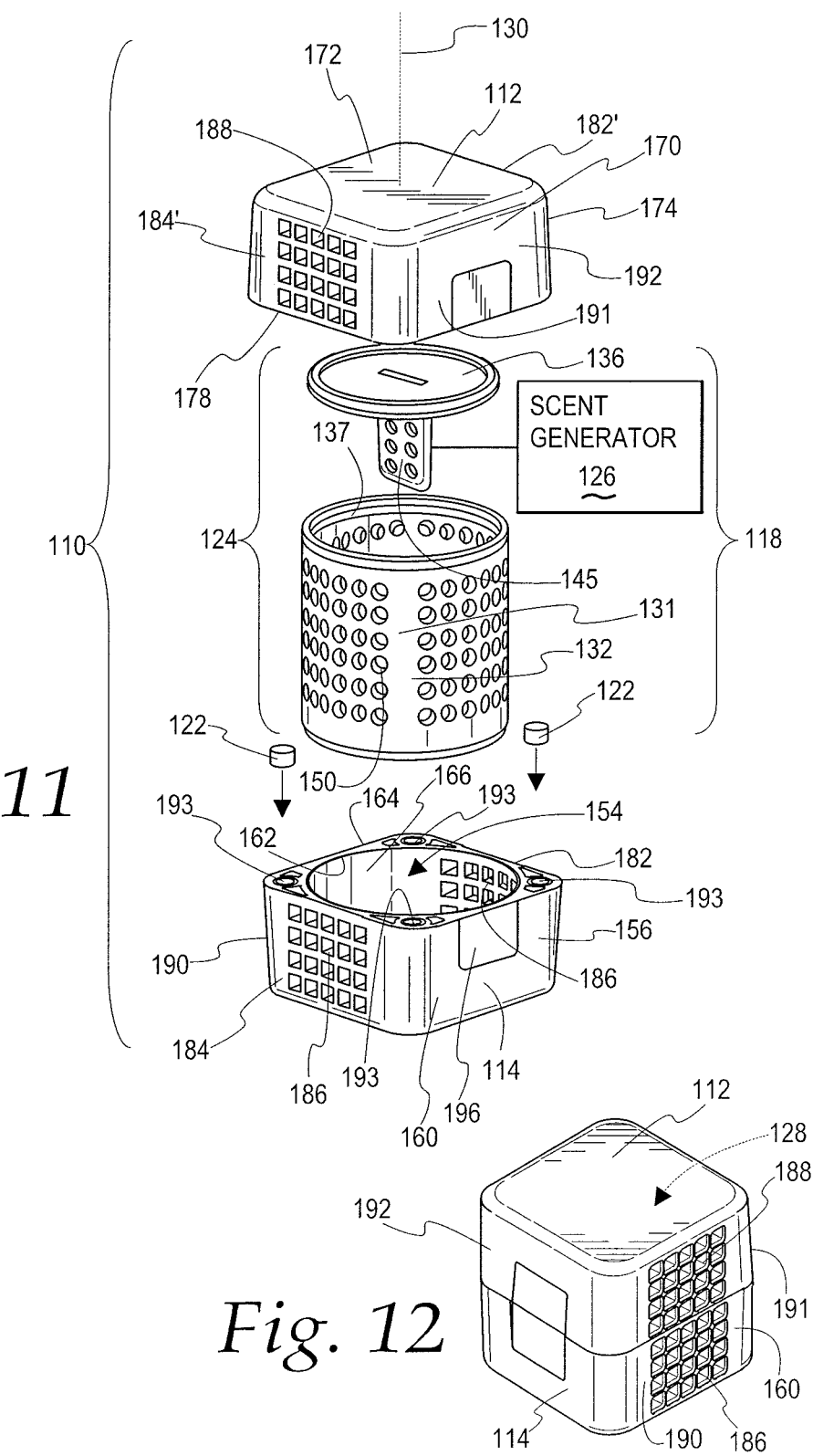

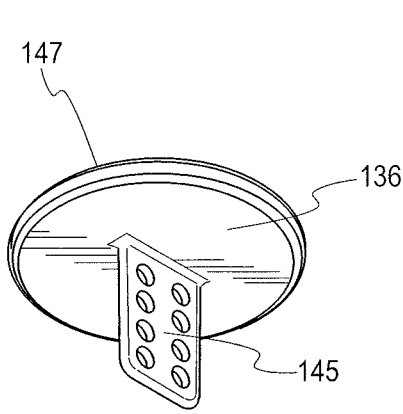 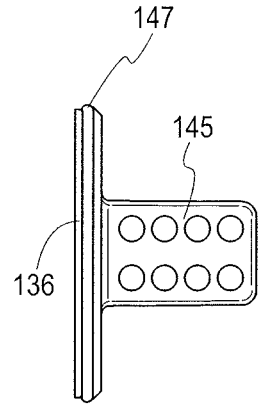
Fig. 23    Fig. 24
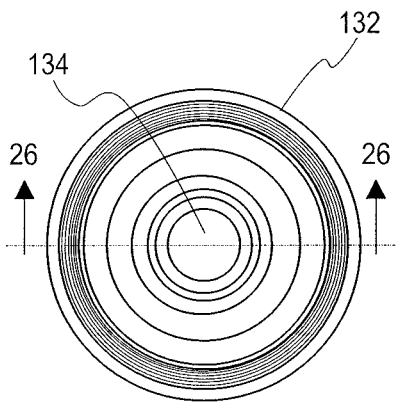
Fig. 25
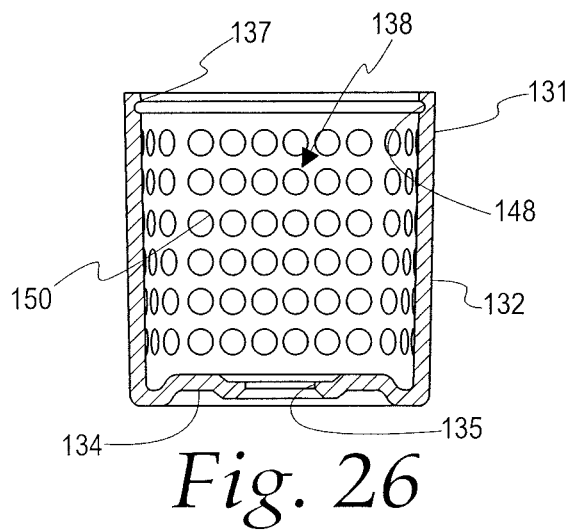
Fig. 26

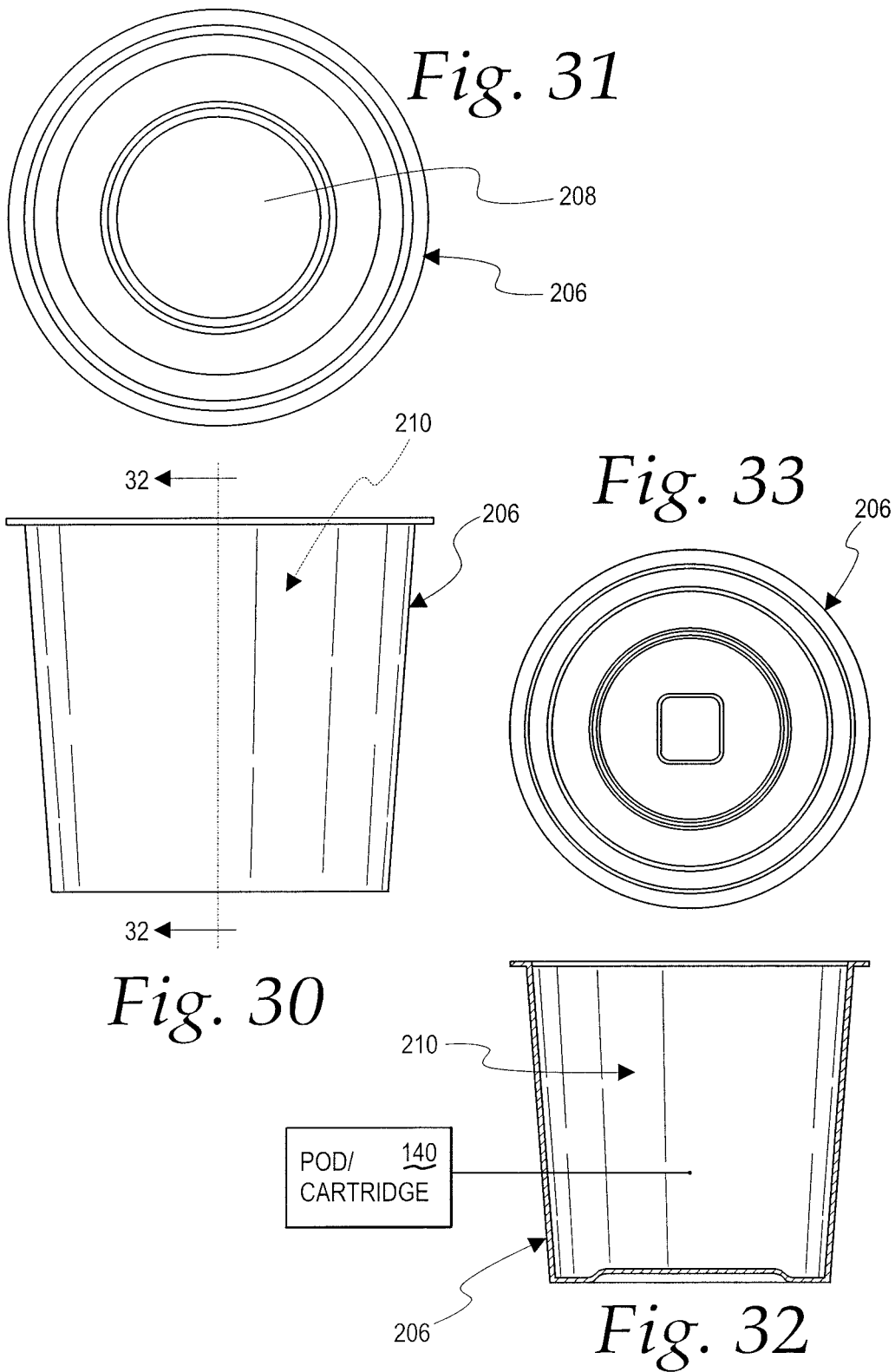

APPARATUS FOR DEODORIZING A SPACE AND METHOD OF USING THE APPARATUS

CROSS-REFERENCE TO RELATED APPLICATIONS

This application is a continuation-in-part of U.S. patent application Ser. No. 17/005,689, filed Aug. 28, 2020, which is a continuation-in-part of U.S. patent application Ser. No. 15/964,849, filed Apr. 27, 2018, which claims priority to U.S. Provisional Patent Application No. 62/491,747, filed Apr. 28, 2017.

BACKGROUND OF THE INVENTION

Field of the Invention

This invention relates to portable deodorizing apparatus of the type that incorporate a source of a scent and from which the scent can be continuously diffused into a space.

Background Art

A multitude of portable deodorizing apparatus are currently commercially available. "Deodorizing", as used throughout the description and claims herein, is intended to encompass delivery of scent that is of a nature to either: a) diminish or dominate an undesired scent in a space; or b) introduce a desired scent into a space that is relatively scent neutral.

Commonly, apparatus of this type are designed for a particular application. For example, deodorizers used in passenger vehicles are commonly in the form of sheets, impregnated with a scent-generating composition and suspended by strings, as from rearview mirrors. This allows for passive diffusion of scent from the composition continuously until the composition is depleted, as by evaporation.

Many different deodorizing apparatus are made with a generally spherically-shaped housing within which a deodorizing source is placed. This design is generally intended to roll, as when used in gym bags, in shoes, in drawers, etc. This spherical design is generally practical only in small, confined volumes.

In larger spaces, it is common to use systems that are more "active" in nature and that may rely on some air movement to force scent into a larger volume. For example, some designs spray a deodorizing composition in mist form at selected intervals. Most existing apparatus that are in the "passive" category do not lend themselves to use in larger spaces, and if so targeted, are often of a size that they are obtrusive and unsightly. Even larger, passive versions generally lack the ability to effect high enough scent diffusion volume to be practical for this application.

Many existing designs are made so that a scent generator can be replenished. Commonly, parts must be disconnected to accomplish this; often requiring reshaping or reconfiguring of one or more of the parts. Often, these designs are lightweight and flimsy such that parts thereof are prone to failing. Some designs are not user friendly and persons often forego the challenge of re-loading a scent generator and opt for disposal after a single use.

Further, many existing designs that use releasably connectable parts—commonly mold formed—require complex shapes and several different parts that elevate mold and manufacturing costs, which reflects in what consumers must ultimately pay.

Most existing apparatus lack versatility and are designed for a specific environment and use. Thus, if one is interested in distributing a scent in a wide range of different environments, he/she must generally purchase a range of different apparatus, each customized for a limited practical use.

The industry continues to seek affordable apparatus in this category that are versatile enough to be used in different environments, ranging from small containers, such as gym bags, lockers, closets, etc., to larger volumes, such as partitioned occupiable spaces or more open spaces, such as in open building lobbies. In addition to this versatility, desired design objectives are also to afford an apparatus that is easy to handle, aesthetically desirable, affordable, and ideally capable of being renewed by replenishing a scent generator repeatedly with a durable foundational structure.

SUMMARY OF THE INVENTION

In one form, the invention is directed to a portable deodorizing apparatus including: a housing having first and second releasably joinable parts; and a deodorant source. The first housing part has at least a first connector. The second housing part has at least a second connector. The at least first connector and the at least second connector are configured to be: a) engaged so as to thereby maintain the first and second housing parts in an operative relationship as an incident of relatively moving the first and second housing parts from a starting relationship, separated from each other, into the operative relationship; and b) disengaged as an incident of relatively moving the first and second housing parts with the first and second housing parts in the operative relationship, so as to thereby allow the first and second housing parts to be changed from the operative relationship into the starting relationship. The first and second housing parts and deodorant source are configured so that with the first and second housing parts in the operative relationship the deodorant source is maintained in an operative position wherein deodorant from the deodorant source is diffused into a space within which the deodorizing apparatus is placed.

In one form, the at least first connector and the at least second connector are magnetically attracted to each other. As an incident of moving the first and second housing parts from the starting relationship into the operative relationship, a magnetic attraction force is generated between the at least first connector and the at least second connector tending to: a) urge the first and second housing parts towards the operative relationship; and b) maintain the operative relationship of the first and second housing parts.

In one form, with the first and second housing parts in the operative relationship and the deodorant source in the operative position, the deodorant source is captive between the first and second housing parts.

In one form, the deodorant source has a housing and a scent generator supported by the housing. The deodorant source housing and one of the first and second housing parts are configured so that the deodorant source housing is movable guidingly relative to the one of the first and second housing parts along an axis.

In one form, the first and second housing parts are relatively movable along the axis in changing between the starting relationship and the operative relationship.

In one form, the first and second housing parts have the same configuration.

In one form, the first and second housing parts each has a cup shape opening in an axial direction with the first and second housing parts in the operative relationship. The first housing part has a first edge extending around the axis and the second housing part has a second edge extending around the axis. With the first and second housing parts in the operative relationship, the first and second edges are one of: a) abutted to each other; and b) adjacent to each other. The cup shapes on the first and second housing parts in the operative relationship cooperatively define a receptacle for the deodorant source.

In one form, the deodorant source housing has a peripheral wall extending around the axis with the first and second housing parts in the operative relationship and the deodorant source in the operative position.

In one form, at least one of the first and second housing parts has a peripheral wall extending around the axis and through which at least one opening is formed. With the first and second housing parts in the operative relationship and the deodorant source in the operative position, scent from the scent generator diffuses through: a) at least one opening in the peripheral wall on the deodorant source housing; and b) the at least one opening formed through the peripheral wall on the at least one of the first and second housing parts and into a space in which the portable deodorizing apparatus is located.

In one form, each of the first and second housing parts has a cup shape. With the first and second housing parts in the operative relationship the cup shapes on the first and second housing parts open, each towards the other.

In one form, the at least first connector is at or adjacent to the first edge and the at least second connector is at or adjacent to the second edge.

In one form, each of the first and second connectors is a magnet.

In one form, the scent generator is an evaporative gel.

In one form, the deodorant source housing and first and second housing parts are configured so that the deodorant source housing is movable guidingly relative to each of the first and second housing parts around the axis.

In one form, with the first and second housing parts in the operative relationship and the deodorant source in the operative position, the first and second housing parts and deodorant source housing are relatively movable guidingly, each relative to the other, around a common axis.

In one form, the at least first connector and at least second connector are magnetically attracted to each other. With the first and second housing parts in the operative relationship and the deodorant source in the operative position, one of the first and second housing parts can be moved guidingly relative to the other of the first and second housing parts to thereby relatively move the at least first connector and the at least second connector so as to thereby reduce or eliminate a magnetic attraction force between the at least first connector and the at least second connector to thereby facilitate movement of the first and second housing parts into the starting relationship.

In one form, at least one of the first and second housing parts has a peripheral wall with radially oppositely facing, substantially flat surface portions that facilitate grasping by a user.

In one form, at least one of the radially oppositely facing surface portions has a circumferentially facing edge that facilitates gripping by a user.

In one form, the deodorant source and first and second housing parts are configured so that the first and second housing parts can be changed back and forth between: a) the starting relationship; and b) the assembled relationship without requiring use of tools or separate fasteners.

In one form, the deodorant source and first and second housing parts are configured so that the first and second housing parts can be changed back and forth between: a) the starting relationship; and b) the assembled relationship without requiring changing a configuration of any of the first and second housing parts and the deodorant source.

In one form, the deodorant source is in the form of a first cartridge including a housing and a scent generator on the housing provided further in combination with a second cartridge that is interchangeable with the first cartridge so that the second cartridge can be used: a) when the scent generator on the first cartridge is exhausted; and b) when it is desired to use a scent generator on the second cartridge that is different than the scent generator on the first cartridge.

In one form, the invention is directed to a method of installing the portable deodorizing device described above in a space bounded by a wall surface. The method includes the steps of: fixing one of the first and second housing parts to the wall surface; and with the one of the first and second housing parts fixed to the wall surface, repositioning the other of the housing parts and deodorant source relative to the one of the first and second housing parts to thereby place and maintain the first and second housing parts in the operative relationship and the deodorant source in the operative position.

In one form, the step of repositioning the other of the first and second housing parts and deodorant source is performed without requiring use of tools or separate fasteners and without requiring changing of a configuration of any of the first and second housing parts and the deodorant source.

In one form, the wall surface faces in a downward direction.

BRIEF DESCRIPTION OF THE DRAWINGS

FIG. 4 is an enlarged, perspective view of a deodorizing material/scent generator stabilizer on the deodorizing apparatus of FIG. 1;

FIG. 5 is an enlarged, perspective view of a first element/housing part making up part of a scent cartridge on the deodorizing apparatus of FIG. 1;

FIG. 6 is an enlarged, perspective view of a second element joinable with the first element/housing part in FIG. 5 to define part of the scent cartridge;

FIG. 11 is an exploded perspective view of another form of portable deodorizing apparatus, as shown schematically in FIGS. 9 and 10;

FIG. 12 is a perspective view of the deodorizing apparatus in FIG. 11 in an assembled state;

FIG. 23 is a bottom, perspective view of part of the housing on the deodorant source shown schematically in FIG. 10 and including a stabilizer component for a scent generator;

FIG. 24 is a side elevation view of the housing part shown in FIG. 23;

FIG. 25 is a top view of another part joinable with the part shown in FIGS. 23 and 24 to define the deodorant source housing in FIG. 10;

FIG. 26 is a cross-sectional view of the housing part taken along line 26-26 of FIG. 25;

FIG. 30 is an enlarged, front elevation view of the storage cup in FIG. 29;

FIG. 31 is a top view of the storage cup in FIG. 30;

FIG. 32 is a cross-sectional view of the storage cup taken along line 32-32 of FIG. 30;

FIG. 33 is a top view of the storage cup in FIGS. 29-32 with a cover thereon;

DETAILED DESCRIPTION OF THE PREFERRED EMBODIMENT

Figure 1:
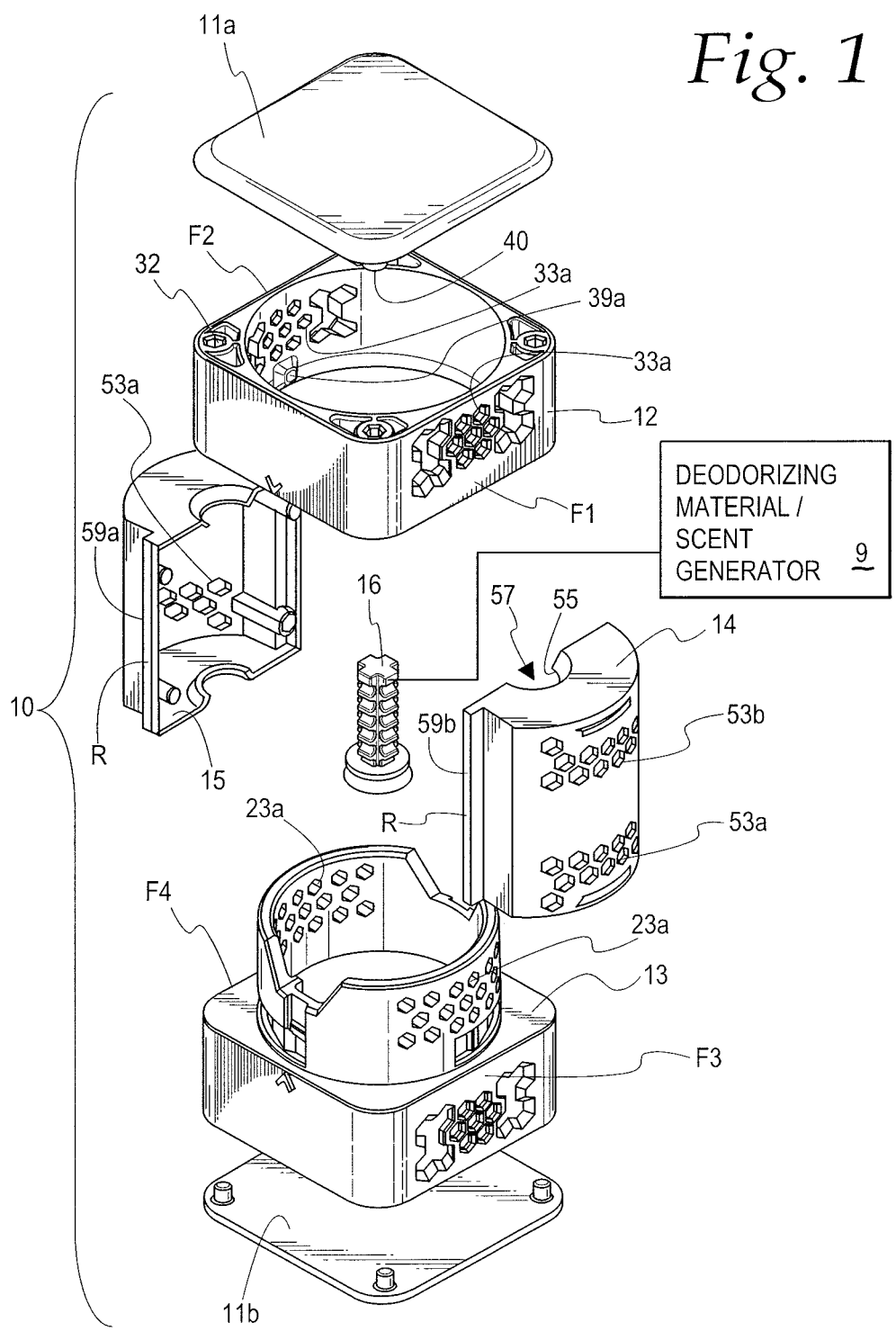
FIG. 1 is an exploded, perspective view of one form of the inventive deodorizing apparatus.

Reference will now be made in detail to several embodiments of the invention that are illustrated in accompanying drawings. Whenever possible, the same or similar reference numerals are used in the drawings and the description to refer to the same or like parts or steps. For purposes of convenience and clarity only, directional terms such as top, bottom, left, right, up, over, above, below, beneath, rear, and front, may be used with respect to the drawings. These and similar directional terms are not to be construed to limit the scope of the invention in any manner. The words attach, connect, couple, and similar terms with their inflectional morphemes do not necessarily denote direct or intermediate connections, but may also include connections through mediate elements or devices.

For purposes of this application, there are primarily two methods for remediating the odors associated with sweat, dirt, etc., such as, but not limited to, that accumulated as by athletic wear and other equipment during exercise. The first method is to introduce a chemical/composition which will chemically neutralize the odor-causing compounds, either by chemically reacting with them in such a way to produce compounds which are not (as) odiferous, or by chemically bonding with them to prevent their dispersal and circulation through the air. Chemical neutralization of the actual odor-causing compounds by either method will be referred to herein as deodorizing with a deodorizer. The second method is to introduce a chemical with a pleasant scent which will mask, cover up, or otherwise distract from and/or overpower the scent of the odor-causing compounds. This will be referred to herein as masking odors with a masking scent. Any given substance used for purposes of the invention may be and/or contain a deodorizer, a masking scent, or both. Thus, references to a "scent", deodorizer", etc. throughout the detailed description and claims should be construed generically to cover any substance that deodorizes, masks, neutralizes, etc., whether or not a residual scent is generated.

Significantly, while initially discussion addresses odors associated with athletic wear, this is simply one exemplary use for the invention. It is contemplated that the invention can be used/practiced in any environment wherein odor is to be addressed or a scent is to be introduced with treatment volume ranging from a small enclosed space, such as a drawer, locker, portable bag, etc., to a large open space, as in a residence, a hotel, an office building, etc.

With reference initially to FIGS. 1-8, the configuration and function of one exemplary form of the invention may be clearly understood. The portable deodorizing device 10 therein consists of, from top to bottom, top cap 11a and top 12, together making up one housing part, a deodorizing cartridge consisting of first cartridge element 14 and second cartridge element 15 which together define a deodorizing source housing and enclose deodorizing material stabilizer 16 and a deodorizing material/scent generator 9, and bottom 13 and bottom cap 11b, which together make up another housing part. The elements 14, 15, stabilizer 16, and deodorizing material 9 collectively make up a deodorizing source/cartridge, identified also hereinbelow as a "pod". When assembled, vent holes/openings 33a in the exterior of device 10 either allow the interior of the deodorizing cartridge to communicate with the outside air (the device then said to be "activated") or do not allow this (the device then said to be "deactivated.") When the device is activated, the deodorizing material/scent generator 9 performs its desired function and either masks odors in the vicinity, deodorizes air and objects in the vicinity, or both. When the device is deactivated, little or no such deodorizing or masking occurs. The function of each individual element of the device will be further explained below.

It should be noted that top cap 11a and bottom cap 11b shown are physically identical. It is optional, but neither preferred nor required, to have the caps be distinct, whether for decorative or other purposes. For instance, if the device has images corresponding to a licensed property or likeness, one cap may bear the likeness of an athlete, while the other cap has the team jersey number of that athlete and/or the logo of that athlete's team. It is also optional to use the cap configuration at all: if the cap configuration is not used, it is required that the ends of the top and the bottom which would have been closed by the caps be manufactured so that these ends are closed.

In FIG. 1, the device 10 is in an activated configuration. Faces F1, F2 on the top 12 of the device 10 which include the vents 33a are aligned with bottom faces F3, F4, respectively, indicating that the device 10 is activated and that the vents/openings 33a are aligned with the corresponding vent holes/openings 53a or 53b in the deodorizing cartridge and vent holes/openings 23a on the bottom 13. The alignment indicators 21, 31 (see FIG. 2 and FIG. 3) are also aligned, indicating that the device 10 is both in the "activated" configuration for deodorizing, and that the top and bottom are locked together and cannot be separated because the top bosses 39a, 39b are not aligned with vertical channels 25a, 25b (see FIGS. 2 and 3).

It is preferred, but not required, that the edges and corners of the device (both top 12 and bottom 14 and top cap 11a and bottom cap 11b) be slightly rounded so as to avoid scratching, ripping, or otherwise damaging athletic apparel or equipment in a bag or other container, the bag or other container itself, or any other object in the vicinity, regardless of environment. The rounded edges and corners also make the device 10 comfortable to grasp. This also makes it less likely that the device 10 will catch on things and be damaged itself.

Figure 2:
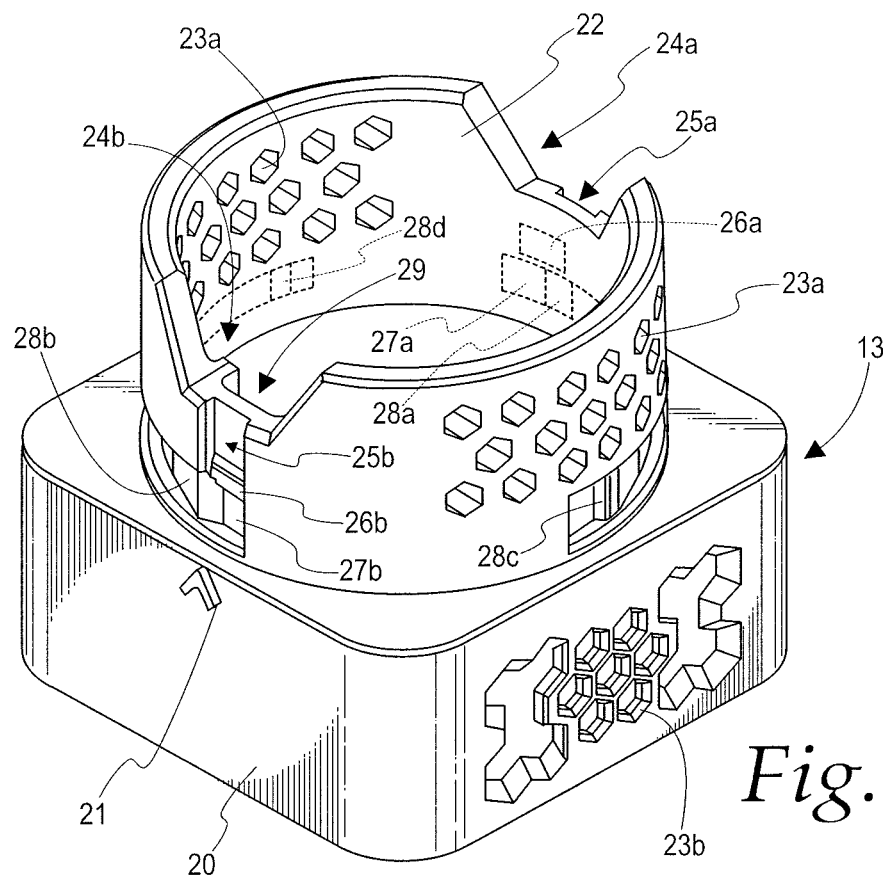
FIG. 2 is an enlarged, perspective view of one housing part/element on the deodorizing apparatus of FIG. 1.

FIG. 2 shows the configuration of bottom 13. Bottom 13 includes base 20 and vertical column 22. The exterior of base 20 is visible when the device is assembled, and vertical column 22 is inserted into cavity 34 of top 12 (see FIG. 3). Bottom interior vents 23a communicate with the interior of the device: when the device is activated, they will line up with vents 53a or vents 53b, depending on which way the deodorizing cartridge is inserted (see FIG. 5) and top vents 33a, providing communication between the interior of the device where the deodorizing material is contained and the outside air. Bottom exterior vents 23b, together with diametrically opposite vents that are not seen in the drawings, are blind vents which do not communicate with the interior of the device and are provided for reasons of visual symmetry. It is preferred that bottom exterior vents 23b be blind vents so that the device can be fully activated and fully deactivated by proper alignment of the top and bottom, but if it is desired for there to always be some communication between the interior of the device and the outside air, they can be through vents. This will result in less deodorizing activity when the device is in the "deactivated" alignment and more when it is in the "activated" alignment, but there will always be some deodorizing activity. It is optional to include bottom exterior vents at all.

Vertical column 22 includes cutouts 24a and 24b, the "notches" in the walls of the vertical column, which allow the user to more easily grip the deodorizing cartridge to remove it for refilling. (See FIG. 1.) It is helpful to include some equivalent of the cutouts as otherwise it can be difficult to remove the deodorizing cartridge if it gets canted or debris gets between the interior of bottom 13 and the deodorizing cartridge and makes it difficult for the cartridge to slide out of the vertical column. On the interior of vertical column 22 is rail guide 29, a vertical channel which allows the rail R formed when the deodorizing cartridge is assembled (see FIGS. 5-7) to lock the deodorizing cartridge into position and stop it from rotating. It is preferred that there be some means for preventing the deodorizing cartridge from rotating with respect to base 13 so that the vents will all line up correctly when the device is activated or deactivated.

On the exterior of vertical column 22 are vertical channels 25a and 25b. Each vertical channel ends at a vertical boss 26a, 26b. The vertical bosses partially interrupt the communication between the vertical channels and horizontal channels. Below each vertical boss 26a, 26b is a horizontal channel 27a, 27b. Proceeding to viewer left along each horizontal channel 27, each horizontal channel 27 is interrupted twice by first horizontal bosses 28a, 28b, and second horizontal bosses 28c, 28d leaving enough free space at the beginning of each horizontal channel and at the end of each horizontal channel for the corresponding top boss to interlock with the beginning or the end of the horizontal channel and the corresponding horizontal boss.

Both the vertical and the horizontal bosses interrupt, but do not completely block, the corresponding channels. It is required that the vertical and horizontal bosses leave enough clearance in the corresponding channels to allow the top bosses to clear them with the application of a reasonable amount of force by the user.

Bottom alignment indicator 21 is optional, but it or some equivalent is preferred. When bottom alignment indicator 21 is aligned with top alignment indicator 31 (see FIG. 3) the user knows both that the device is activated, and that the top and the bottom cannot be separated for refilling purposes by pulling them apart and overcoming the friction/elastic resistance of top bosses 39a, 39b against base vertical boss 26a, 26b. When the bottom alignment indicator and the top alignment indicator are on tangent faces and not aligned, the user knows that the device is deactivated, and that the top and bottom can be separated for refilling purposes. Alternate methods of indicating alignment/activation status can also be used, such as corresponding colors or patterns on the faces which show when the device 10 is in a particular configuration. For instance, corresponding upper and lower halves of the word "DEOBLOCK" are visible on other faces of the device: when the word is complete, the user knows that the device is activated. Similar arrangements could be made to show deactivated status. Such indication is preferred, but not required, as the user can always simply try to open the device 10 by using trial and error and/or closely inspect the vent holes to see if they are open to the interior of the device.

Figure 3:
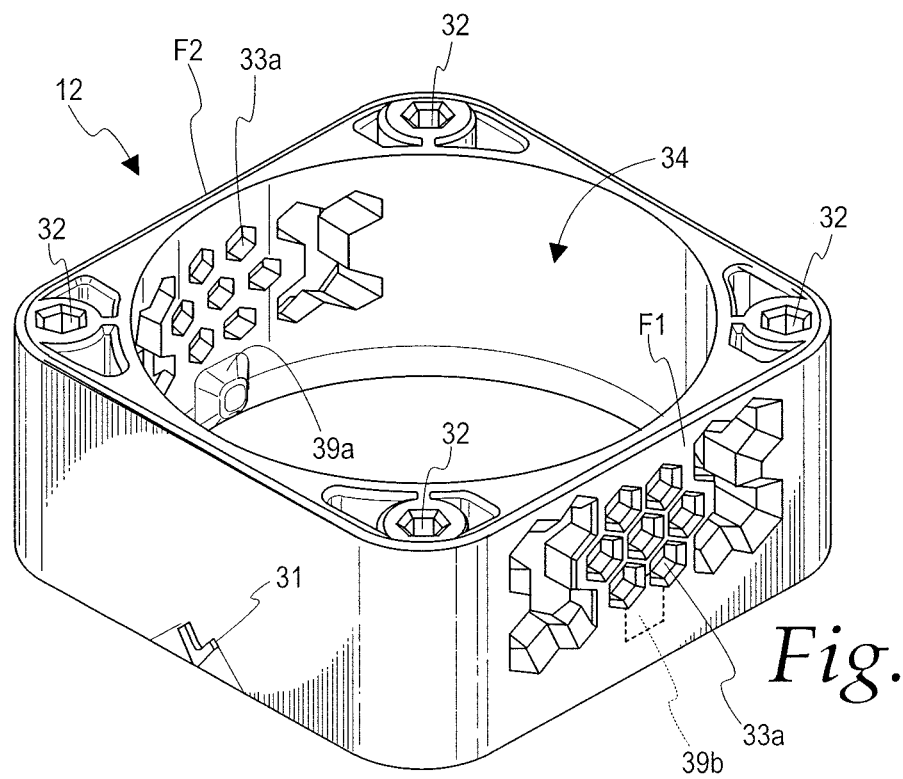
FIG. 3 is an enlarged, perspective view of another housing part/element joinable to the housing part in FIG. 2.

FIG. 3 shows the configuration of the top of the device. Top 12 has receivers 32 for pressure-fitted mounting elements 40 of top cap 11a (see FIG. 1). Top vents 33a allow the interior of the device to communicate with the external air. When the device is in the activated configuration, top vents 33a align with bottom interior vents 23a and vents 53a or 53b as previously described, allowing for deodorizing activity. When the device is in the deactivated configuration, top vents 33a do not so align, and there is no, or limited, deodorizing activity (but see alternate configuration described above). Vertical column 22 (see FIG. 2) is inserted into cavity 34 of top 12, and top 12 rotates relative to base 20 (see FIG. 2) with vertical column 22 serving as the "axle" of such rotation.

Top 12 has two diametrically opposite top bosses 39a, 39b. To assemble the device, top 12 is aligned with bottom 13 such that cavity 34 can slide over vertical channel 22. Each top boss 39 is aligned with a vertical channel 25, so that each top boss can slide into the corresponding vertical channel. The first obstacles that the top bosses encounter are the corresponding vertical bosses 26; until the top bosses are slid past the vertical bosses by application of sufficient force on top 12, top 12 and bottom 13 can be easily separated. Once the top bosses are slid past the vertical bosses, the top and bottom are in a position corresponding to the "deactivated" configuration. The top will not easily separate or move vertically due to the interaction between the top boss and the vertical boss in each horizontal channel, and it will not easily turn to viewer left due to the interaction between the top boss and the first horizontal boss 28a, 28b in each horizontal channel.

To activate the device, the top is rotated to viewer left relative to the bottom. Once past the first horizontal boss, the top boss will encounter the second horizontal boss 28c, 28d in each horizontal channel. With sufficient torque, the user can rotate the top such that the top boss moves over and past the second horizontal boss, resulting in the top boss being trapped between the second horizontal boss and the end of the horizontal channel. This position corresponds to the "activated" configuration. The top will not move vertically as there is nowhere for the top boss to go, and it will not easily move horizontally due to the interaction between the top boss and the second horizontal boss in each horizontal channel. The vents in the top and bottom are aligned, allowing the deodorizing material to act on outside air as it flows in and out through the vents.

To deactivate the device, the top is rotated back to the position where the top bosses are at the other end of the horizontal channels, trapped between the first horizontal bosses and the end of each horizontal channel. The vents are not aligned and outside air cannot flow in and out of the deodorizing cartridge, stopping the deodorizing process. Although the top can now be disengaged from the bottom, it will stay in the deactivated position unless sufficient force is applied to pull the top bosses over the vertical bosses.

FIG. 4 shows the configuration of the deodorizing material stabilizer 16. In the preferred embodiment, the deodorizing material/scent generator 9 is a gel, solid, or semi-solid material which fills or partially fills the deodorizing cartridge. If the deodorizing cartridge is simply partially or entirely filled with deodorizing material, the material can break loose (especially as such materials tend to shrink as they work) and may be broken into smaller and smaller pieces, some of which may escape through the vents, or block them and reduce the circulation of the air and hence the deodorizing activity. It is preferred to use the deodorizing material stabilizer as shown to minimize the movement of the deodorizing material.

Deodorizing material stabilizer 16 consists of head 41 and shaft 43. Head 41 has groove 40 which engages flanges 55 (see FIGS. 5 and 6) of the deodorizing cartridge elements so that when the deodorizing cartridge is assembled, deodorizing material stabilizer 16 is locked into position. Along the shaft are ridges 42 which define cavities 44. When the deodorizing cartridge is filled, the ridges and cavities provide both additional surface area for engagement and a physical engagement which tends to retain the deodorizing material in place. It is preferred to use ridges 42 or some equivalent thereof which are not continuous like a screw thread, which minimizes the opportunity for the deodorizing material to work its way loose.

It is preferred, but not required, that shaft 43 not be as long as the entire interior length of the deodorizing cartridge, to provide increased volume for deodorizing material.

Figure 7:
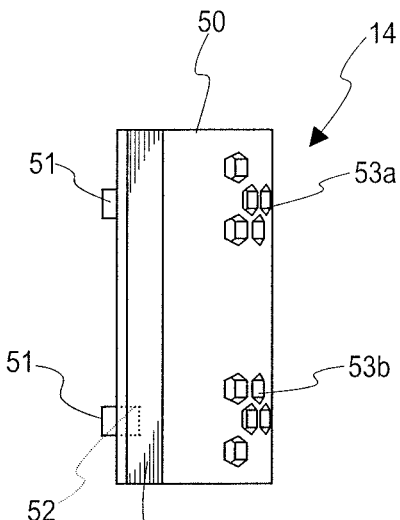
FIG. 7 is a side elevation side view of the first element/housing part in FIG. 5.

FIGS. 5 and 7 show the first cartridge element 14. It should be noted that in the preferred embodiment, the cartridge elements are mirror images of each other but otherwise identical for purposes of this application. This does not apply to non-functional features such as decoration or indicator markings. Optional flat area 54 allows an easier grip when the deodorizing cartridge is to be removed for refilling or replacement. Main portion 50 is cylindrically shaped and fits into the interior of vertical column 22 and cavity 34 such that top 12 can freely rotate and tightly interface with bottom 13. It is preferred that the length of the cartridge elements is approximately the same as the interior length of vertical column 22 such that the deodorizing cartridge cannot move vertically when the device is assembled.

Cartridge element bosses 51 interact with cartridge element boss receivers 52 (see FIG. 6) such that the cartridge elements can be press-fitted together and forced into symmetrical alignment. Vents 53a and 53b communicate between the interior and exterior of the deodorizing cartridge such that the external air can circulate around the deodorizing material when all of the vents are aligned (in the "activated" configuration) so that deodorizing activity will occur. While it is optional to include vents 53b, it is preferred to include both so that no matter which way the deodorizing cartridge is inserted, the vents will align when the device is activated. If vents 53b are not included it is required that the deodorizing cartridge be inserted such that vents 53a are aligned with the bottom interior vents 23a when the device is activated.

End openings 57 are defined and surrounded by flanges 55. One end opening will be filled by the head of the deodorizing material stabilizer (see FIG. 4). The other will be open, but if the deodorizing cartridge is configured as described in the preferred embodiment, it will be sealed by the corresponding cap (see FIG. 1).

Rail boss 59a forms the rail (along with the corresponding rail boss 59b on the second cartridge element) which goes into rail channel 29 to keep the deodorizing cartridge aligned and keyed into position.

It is preferred, but not required, that the exterior corners of the rail be tangent to the circle defined by the exterior of the main portion of the deodorizing cartridge. If the deodorizing cartridge sleeve 60 (see FIG. 8) is to be used, it is required that the exterior corners of the rail either be tangent to the circle defined by the exterior of the main portion of the deodorizing cartridge or be located inside it so that the deodorizing cartridge sleeve fits properly.

FIG. 6 shows the configuration of the cartridge element bosses and cartridge element boss receivers. Second cartridge element has cartridge element boss 51 which engages the corresponding cartridge element boss receiver on the first cartridge element, and cartridge element boss receiver 52 which engages the corresponding cartridge element boss on the first cartridge element. It is preferred, but not required, that the cartridge element bosses and cartridge element boss receivers be symmetrically distributed as shown.

FIG. 7 shows an alternate view of the first cartridge element, with the vents 53a and 53b, main portion 50, cartridge element boss 51, and cartridge element boss receiver 52.

Figure 8:
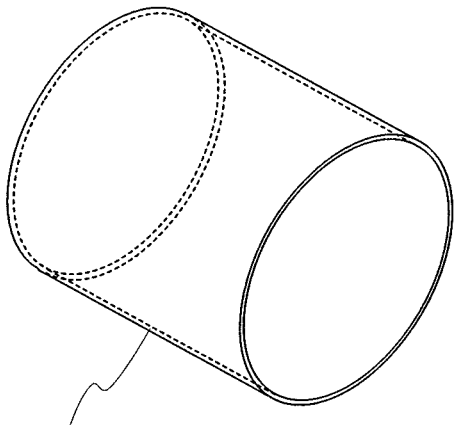
FIG. 8 is a perspective view of a sleeve to cover the scent cartridge including the joined first and second elements/housing parts in FIGS. 5-7.

FIG. 8 shows an optional deodorizing cartridge sleeve 60. In the preferred embodiment, the deodorizing material stabilizer is inserted between the deodorizing cartridge elements such that the head of the deodorizing material stabilizer blocks one end opening. Sleeve 60 is the same length as the assembled deodorizing cartridge and has an interior diameter that will closely surround the exterior diameter of the main portion of the deodorizing cartridge. The deodorizing cartridge is placed within sleeve 60 and the deodorizing material, in liquid or semi-liquid form, is inserted into the deodorizing cartridge through the other end opening. The deodorizing material cannot escape through the vents, as they are blocked by the sleeve. Once the deodorizing cartridge is filled to the desired level, the entire assembly is shrink-wrapped, taped, or otherwise secured so that the deodorizing material cannot escape if the device is tilted and the sleeve will not slide off the deodorizing cartridge until the device is ready for use. Before that time, the deodorizing material will harden to the point where it will not flow out of the vents or the open end of the deodorizing cartridge. When the device is ready for use, the user simply removes the seal and the sleeve, inserts the deodorizing cartridge into the device, and activates it.

Among the many objectives of the present invention is the provision of a device which can ameliorate the development of perspiration-related odor as in bags and other containers where athletic equipment is stored, as well as other confined spaces and potentially open spaces.

Another objective of the present invention is the provision of a device which can ameliorate the development of perspiration-related odor where rough handling is a possibility, without being easily damaged.

Yet another objective of the present invention is the provision of a device which can ameliorate the development of odors, such as perspiration-related odors and can be easily and visibly activated, deactivated, and refilled.

These and other objectives of the invention (which other objectives become clear by consideration of the specification and drawings as a whole) are met by providing the device as described above and in further embodiments described hereinbelow for controlling odor and/or introducing a scent into a closed or an open volume.

Figure 9:
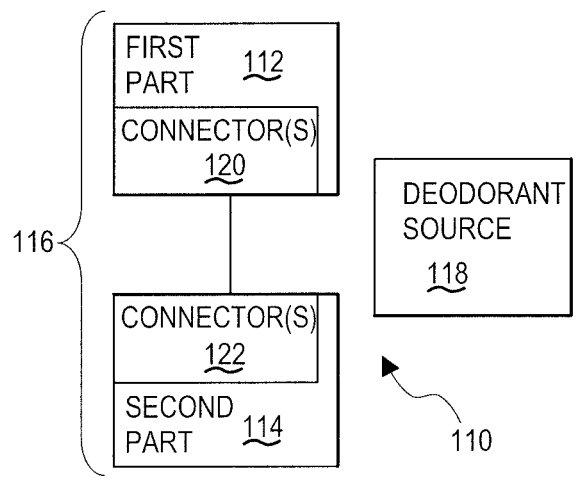
FIG. 9 is a schematic representation of a portable deodorizing apparatus, according to the invention.

A schematic representation of a portable deodorizing apparatus, according to the present invention, is shown at 110 in FIG. 9. The schematic depiction encompasses the forms of the device/apparatus, described above, and additional forms thereof including, but not limited, to those described below. The apparatus 110 is made up of a first part 112 and a second part 114 that are joined to define a housing 116. The deodorizing apparatus further has a deodorant source 118.

The first housing part 112 has at least a first connector 120, with the second housing part 114 having at least a second connector 122.

The at least first connector 120 and at least second connector 122 are configured to be engaged so as to thereby maintain the first and second housing parts 112, 114 in an operative relationship as an incident of relatively moving the first and second housing parts from a starting relationship, such as wherein they are fully separated from each other, into the operative relationship.

The schematic depiction of the components in FIG. 9 is intended to encompass virtually an unlimited number of variations of each of the components and their interaction. As just one example, the connectors 120, 122 may be configured so that upon being engaged the housing parts 112, 114 cannot be separated from each other without being modified or destroyed.

Alternatively, and in one preferred form, as described for the embodiments hereinbelow, the connectors 120, 122 and housing parts 112, 114 are configured so that with the connectors 120, 122 engaged and the housing parts 112, 114 in the operative relationship, the connectors 120, 122 can be readily disengaged so as to thereby allow the first and second housing parts 112, 114 to be changed from the operative relationship into a starting relationship—partially or fully separated from each other.

In one preferred form, this disengagement of the connectors 120, 122 is effected by relatively moving the first and second housing parts 112, 114, starting with the first and second housing parts 112, 114 in their operative relationship.

In one preferred form, changing between the operative and starting relationships may be effected simply by relatively moving the housing parts without requiring tools, separate fasteners, or changing a configuration of any part of either of the housing parts 112, 114.

The first and second housing parts 112, 114 and deodorant source 118 are configured so that with the first and second housing parts 112, 114 in the operative relationship, the deodorant source 118 is maintained in an operative position wherein deodorant from the deodorant source 118 is diffused into a space within which the deodorizing apparatus 110 is placed.

Some specific exemplary forms of the deodorizing apparatus will now be described, with it being understood that these embodiments, which come within the schematic depiction in FIG. 9, are exemplary in nature only as virtually an unlimited number of variations thereof are contemplated.

Figure 10:
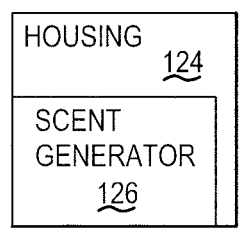
FIG. 10 is a schematic representation of a deodorant source on the deodorizing apparatus in FIG. 9 and showing additional details thereof.
Figure 13:
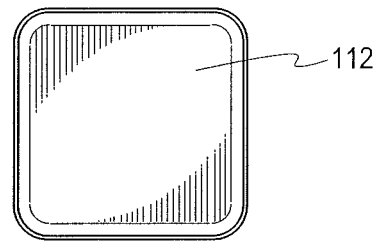
FIG. 13 is a top view of the deodorizing apparatus shown in FIGS. 11 and 12.
Figure 14:
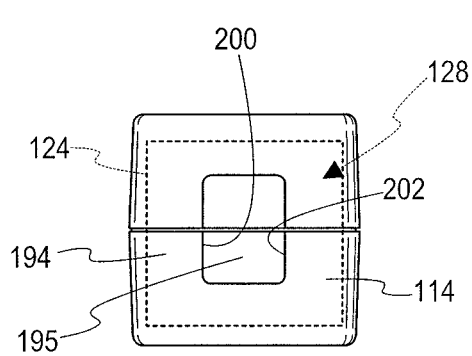
FIG. 14 is a side elevation view of the deodorizing apparatus shown in FIGS. 11-13.
Figure 15:
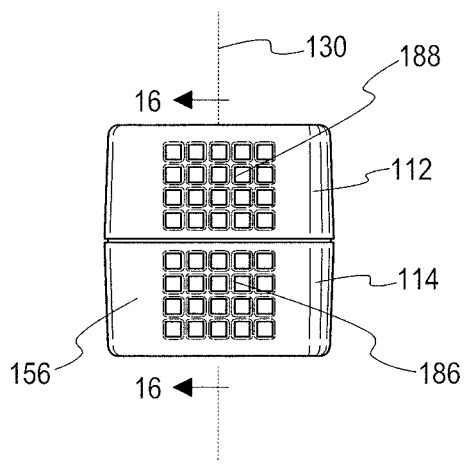
FIG. 15 is a front elevation view of the deodorizing apparatus shown in FIGS. 11-14.
Figure 16:
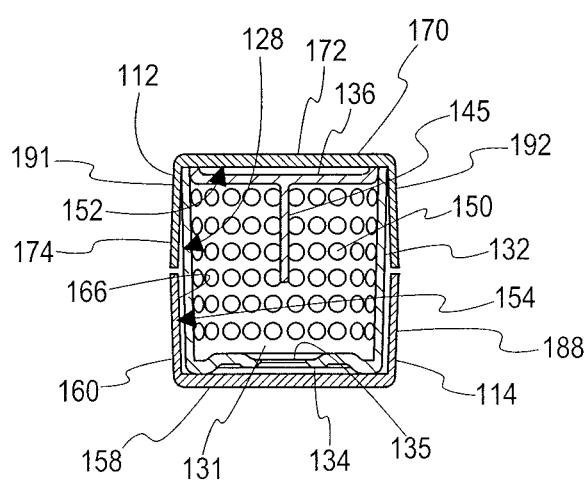
FIG. 16 is a cross-sectional view of the deodorizing apparatus taken along line 16-16 of FIG. 15.
Figure 17:
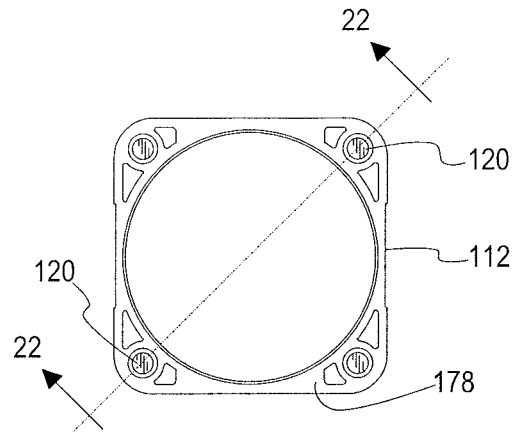
FIG. 17 is a bottom view of an upper one of two joinable housing parts on the deodorizing apparatus in FIGS. 11-16.
Figure 18:
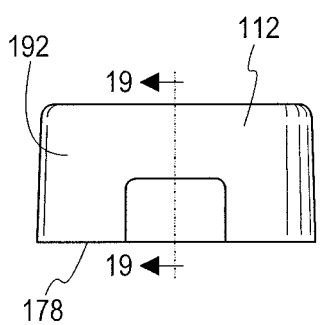
FIG. 18 is a side elevation view of the housing part in FIG. 17.
Figure 19:
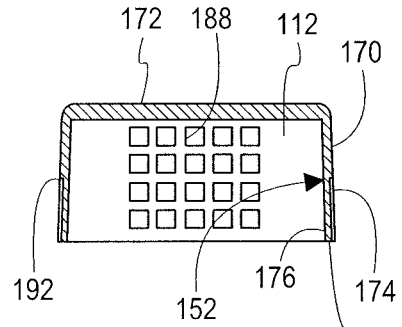
FIG. 19 is a cross-sectional view of the housing part taken along line 19-19 of FIG. 18.
Figure 20:
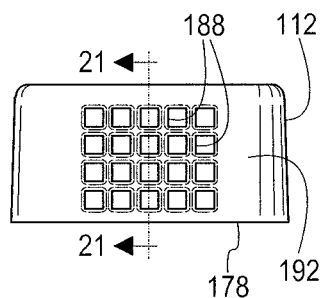
FIG. 20 is a front elevation view of the housing part shown in FIGS. 17-19.
Figure 21:
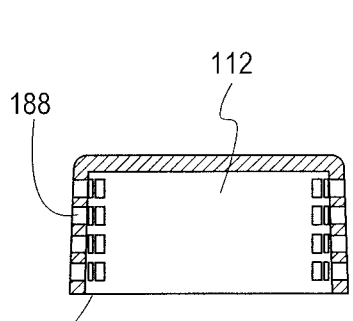
FIG. 21 is a cross-sectional view of the housing part taken along line 21-21 of FIG. 20.
Figure 22:
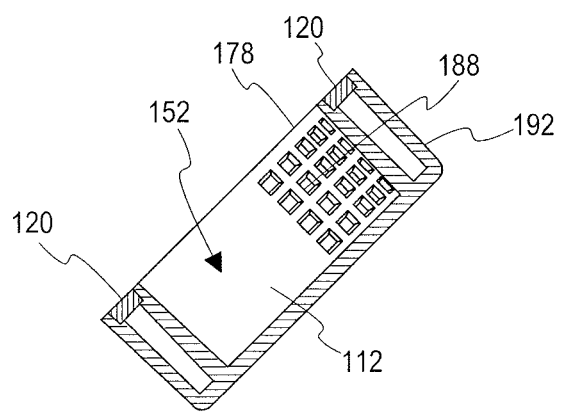
FIG. 22 is a cross-sectional view of the housing part taken along line 22-22 of FIG. 17.

In one exemplary form, as shown schematically in FIG. 10, the deodorant source 118 consists of a housing 124 with a scent generator 126 supported by the housing 124. As described above, the scent generator 126 may take any form, such as a gel, solid, or semi-solid material, and potentially even a liquid form. Preferably, the scent generator 126 is, or becomes, a shape-retentive composition, capable of being integrated into the housing 124.

Referring now to FIGS. 11-36, a specific exemplary form of the deodorizing apparatus 110 is shown to include a first housing part 112 and a second housing part 114 which, in the operative relationship of FIG. 11, cooperatively make up a housing that defines a volume 128 to receive the deodorant source 118.

As noted previously, while the designations "top", "bottom", "side", etc. will be utilized, these designations are arbitrary. For purposes of simplicity and reference only, the FIG. 11 orientation of the deodorizing apparatus 110 is considered to be an upright orientation wherein the deodorizing apparatus 110 has a central vertical axis 130. The axis 130 is significant primarily to describe relationships of elements, as the exposed surface shape of the deodorizing apparatus 110 may have certain symmetrical aspects or may be totally random in shape with respect to the axis 130.

The deodorant source housing 124 is shown with a cylindrical shape having a main body 131 with a peripheral annular wall 132 and an integral bottom wall 134 with a fill opening 135 therethrough. A top wall 136 blocks a top opening 137 formed by the peripheral annular wall 132. The peripheral annular wall 132, top wall 136, and bottom wall 134 cooperatively bound a volume 138 to receive the scent generator 126.

Figure 28:
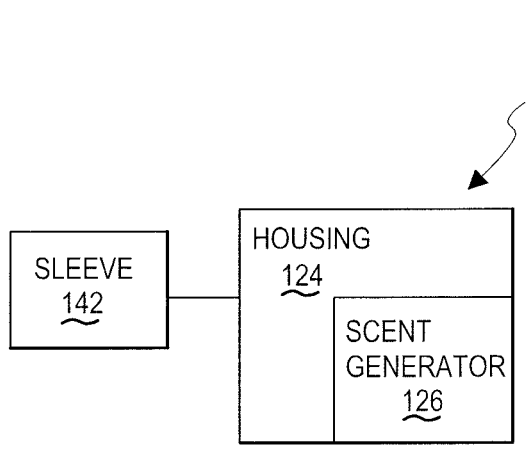
FIG. 28 is a schematic representation of the deodorant source housing as in FIG. 10 within a sealing sleeve.
Figure 29:
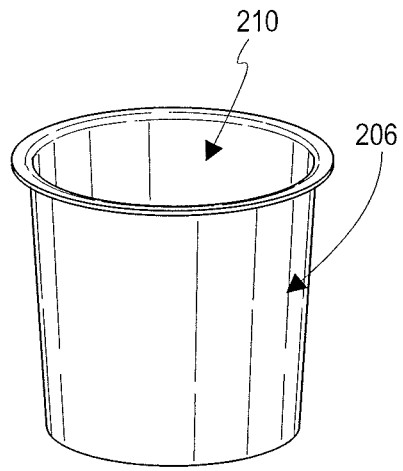
FIG. 29 is a perspective view of a cup that can be utilized to store the deodorant source in a pod form consisting of at least the housing and scent generator as shown schematically in FIG. 10.

In one preferred form, the scent generator 126 is integrated into the housing 124 to form a pod/cartridge, identified schematically at 140 in FIG. 28. A cup-shaped sleeve 142, similar to the sleeve shown in FIG. 8, receives the housing 124 and may be closely dimensionally formed, and/or shrink-wrapped around the housing 124, to overlie the peripheral annular wall 132 and top wall 136 while allowing the composition of the scent generator 126 to be introduced through the bottom fill opening 135, as with the housing 124 inverted, thereby to partially or fully fill the volume 138. A flat stabilizer component 145, depending from the top wall 136, is surrounded by the scent generator 126 to effect stabilization thereof, as with the scent generator in a gel form, as described above.

In a typical process, the scent generator 126 may initially be in a pourable form that is cured to a gel that is shape-retentive and stabilized by the component 145. The stabilizer component is integral with the top wall 136, which has an annular bead 147 that can be snap fit into a complementary receptacle 148 to be firmly held on the peripheral wall 132 to thereby define a self-contained unit, including the scent generator 126, making up the pod/cartridge 140. The sleeve opening through which the scent generator material is introduced may then be closed as by being sealed against itself, or otherwise, to define a sealed or partially sealed construction that reduces, or avoids, evaporation of material, such as a gel, making up the scent generator 126.

The sleeve 142 and pod/cartridge 140 may be dimensioned so that the sealed pod/cartridge 140 can be placed in the operative position with the housing parts in the operative relationship to facilitate handling and storage. Alternatively, the housing parts 112, 114 and sealed pod/cartridge may be handled separately with the sleeve 142 required to be removed before allowing the deodorant source/pod/cartridge 140 to be placed in the operative position.

In the depicted form, the peripheral wall 132 has a plurality of openings 150 therethrough. The openings are arranged at regular intervals in circumferentially and axially spaced relationship. The depicted opening size and arrangement is exemplary in nature only. The purpose of the openings is to allow diffusion of scent from the scent generator 126 in a pattern fully around the axis 130 over preferably a majority of the height of the peripheral wall 132. Any arrangement of openings, including size, shape, and relative position is contemplated so long as there is a wide diffusion path and the integrity of the peripheral wall is adequately maintained. A single, contiguous opening might also be designed.

The peripheral wall 132 has a slightly tapering diameter from top to bottom to facilitate mold formation.

In this embodiment, the housing parts 112, 114 are designed to be moved from the aforementioned starting relationship, in this exemplary case fully separated from each other as in FIG. 11, axially towards each other into the operative relationship of FIGS. 12-16, wherein the pod/cartridge 140 is captive between the housing parts 112, 114.

As depicted, each of the housing parts 112, 114 has a female, cup-shaped, receptacle 152, 154, respectively, complementary to the axially spaced top and bottom of the pod/cartridge 140. The combined volumes of the receptacles 152, 154 make up the aforementioned volume 128.

For the exemplary housing part 114, a body 156 thereon has a generally cup shape with a bottom wall 158 and a peripheral wall 160 projecting upwardly therefrom and having an opening 162 surrounded by a top edge 164.

The peripheral wall 160 has a radially inwardly facing, cylindrical surface 166 that, in conjunction with the bottom wall 158, bounds the receptacle 154 for a bottom portion of the housing 124 on the pod/cartridge 140. The surface 166 depicted has a diameter slightly greater than that of the pod/cartridge 140 and tapers from top to bottom to facilitate guided introduction of the pod/cartridge 140. In the absence of any keying structure, which is optional, the pod/cartridge may be introduced in any angular orientation around the axis 130 and turn guidingly relative to the housing part 114 around the axis 130 through 360°.

The housing part 112 has a body 170 with a top wall 172, a peripheral wall 174 extending downwardly therefrom, and a bottom opening 176 surrounded by a bottom edge 178.

Accordingly, with the housing parts 112, 114 in a starting position, as by being separated as in FIG. 11, and with the pod/cartridge 140 residing therebetween, the housing parts 112, 114 can be moved along the axis 130 towards each other into the operative position of FIGS. 12-16, wherein the pod/cartridge 140 is captured therebetween.

Diametrically opposite wall portions 182, 184 on the housing part 114 have an arrangement of openings 186 therethrough and define communication paths between the receptacle 154 and the surrounding environment. Over portions of each wall portion 182, 184, the openings 186 are regularly spaced both axially and circumferentially. Again, a single, contiguous opening may be designed to perform the desired function.

With the bottom of the pod/cartridge 140 in the receptacle 154, deodorant/scent generated from the scent generator 126 is allowed to diffuse through the openings 150 on the deodorant source housing 124 and thereafter through the openings 186 through the wall portions 182, 184 on the housing part 114.

A similar arrangement of openings 188 is provided on the housing part 112 on corresponding wall portions 182', 184' to perform the same function.

The arrangement of the openings 150, 186, 188 depicted is only exemplary. Any number, size, and shape of the openings 150, 186, 188 may be utilized as dictated by desired diffusion pattern and appearance.

The housing parts 112, 114 and pod/cartridge 140 may be designed so that the pod/cartridge 140 may be inverted to be placed in an alternative operative position and perform in the same manner.

The precise shape of the housing parts 112, 114 is a design consideration. As shown, the peripheral wall 160 on the housing part 114 has a polygonally-shaped outer surface 190 that is matched to an outer surface 191 on a peripheral wall 192, corresponding to the peripheral wall 160.

Accordingly, with the housing parts 112, 114 moved into their operative relationship, the edges 164, 178 come into adjacent or abutting relationship, with the outer surfaces 190, 191 having a matching shape as shown, for example, in FIG. 12.

As previously mentioned, the connector(s) 120 and connector(s) 122 acting between the first and second housing parts may effect a permanent or releasable connection. In one preferred form, the connectors 120, 122 interact through magnetic attraction. This can be achieved by making one of the connectors 120, 122 using a magnetized material and the other of the connectors 120, 122 using a non-magnetized material that would be attracted to the magnetized material, such as a non-magnetized metal piece.

Alternatively, both of the connectors 120, 122 may be magnetized with their poles oriented to attract each other.

Figure 27:
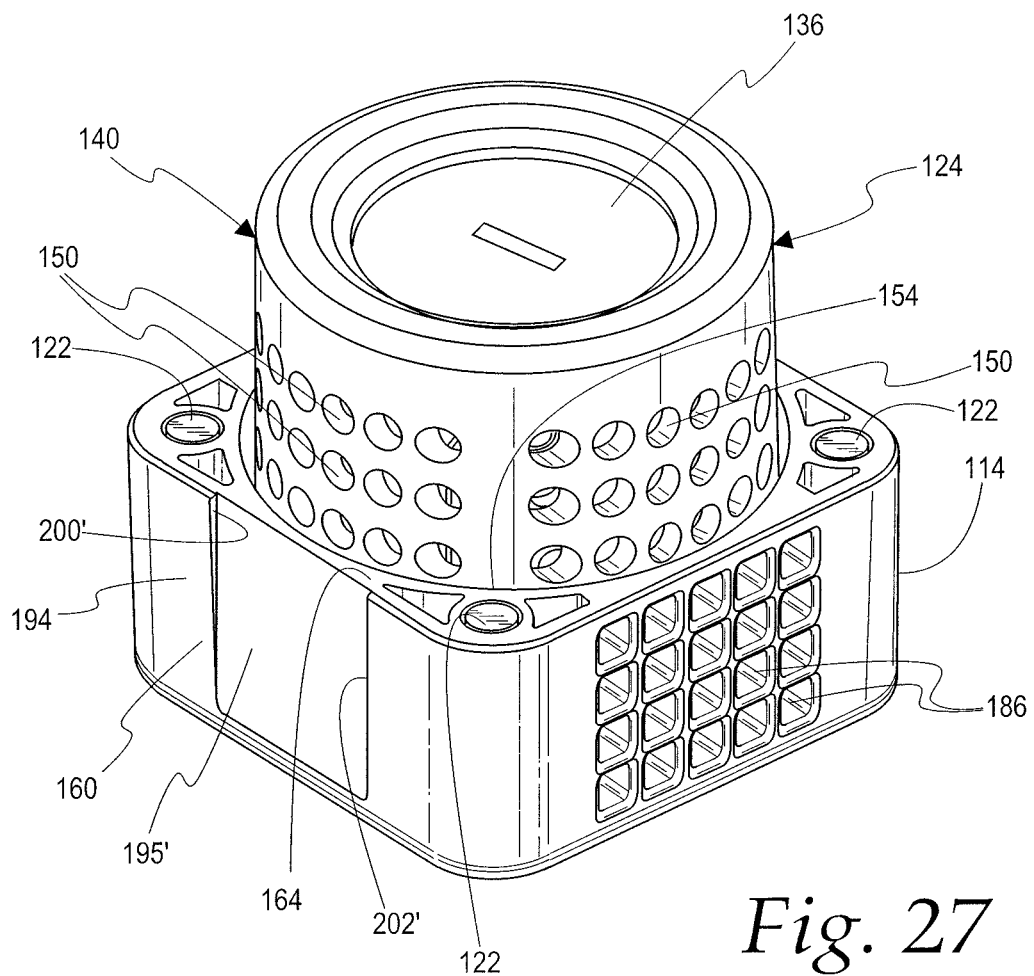
FIG. 27 is an enlarged, perspective view of the housing part in FIGS. 17-22 joined with a deodorant source housing made up of the components shown in FIGS. 23-26.

In one exemplary form, at least one, and as shown preferably two, magnetized connectors are used on each of the housing parts 112, 114. As depicted, magnetized connectors 122 are anchored, as by being press fit and/or adhered within an undercut receptacle 193, at diametrically opposite locations at or adjacent to the edge 164 on the housing part 114. In FIG. 27, four magnetized connectors 122 are shown.

Magnetized connectors 120 are similarly fixed to the housing part 112 at or adjacent the edge 178 at diametrically opposite locations so as to align, one each, with the connectors 122 with the housing parts 112, 114 in their operative relationship.

Receptacles are shown to accommodate four such connectors 120, 122 on each housing part 112, 114.

As an incident of moving the first and second housing parts 112, 114 from a fully separated starting relationship into the operative relationship, a magnetic attraction force is generated between the connectors 120, 122 at diametrically opposite locations tending to: a) urge the first and second housing parts 112, 114 towards the operative relationship; and b) ultimately maintain the operative relationship of the first and second housing parts 112, 114.

In the form depicted, there is no axial projection from either of the housing part edges 164, 178. Accordingly, in the event that the housing parts 112, 114 are relatively angularly misaligned so that the connectors 120, 122 do not directly confront each other as the edges 164, 178 are moved close to each other, the housing parts 112, 114 can be relatively turned around the axis to bring the connector pairs 120, 122 into alignment whereby an attractive force is generated. These attractive forces tend to urge the housing parts 112, 114 into the desired angular alignment as well as maintain the operative relationship between the first and second housing parts.

The ability of the pod/cartridge 140 to guidingly move relative to each of the housing parts 112, 114 both axially along and around the axis 130 facilitates consistent assembly. In the absence of any indexing structure, care need not be taken to angularly align the housing parts 112, 114 around the axis as the assembly process is undertaken. The pod/cartridge 140 functions as an axle and effectively guides the housing parts 112, 114 towards each other until the edges 164, 178 are adjacent to each other, whereupon the housing parts 112, 114 can be relatively turned around the axis 130 to engage the connectors 120, 122. With two pairs of connectors 120, 122, the operative relationship between the housing parts 112, 114 can be arrived at with the housing parts in two different angular relationships achievable by relative angular turning through 180°. With additional connectors 120, 122, further angular relationships between the housing parts 112, 114 can be maintained.

Disassembly is effected with the housing parts 112, 114 in the operative relationship by: a) simply drawing the housing parts axially away from each other to overcome the magnetic attraction forces; or b) relatively turning the housing parts 112, 114 around the axis 130 to bring the connectors 120, 122 out of alignment, whereupon the separation of the housing parts 112, 114 can be more easily effected.

In the depicted form, the housing parts 112, 114 are identical in construction. This, while not a requirement, reduces the number of different parts that must be manufactured. The housing parts 112, 114 can each be made as a single molded piece; though this is not a requirement. As depicted, only three different parts need to be formed, as by molding: a) the housing part 112, 114; b) the main body 131 on the deodorant source housing 124; and c) the snap fit top wall 136.

From an assembly standpoint, a user does not have to be conscious of whether he/she is manipulating the top or bottom housing part 112, 114. Assembly may involve handling only three separate "units"—the first and second housing parts 112, 114 and the pod/cartridge 140.

In the depicted embodiment, the exemplary housing part 114 has diametrically oppositely facing, substantially flat, surface portions 194, 196 that facilitate grasping by a user. The matching peripheral outer surface configuration on the housing part 112 forms a similar gripping arrangement. Multiple flat surfaces on the housing parts 112, 114 facilitate placement on flat surfaces in different orientations.

On the surface portion 194, there is a rectangular undercut 195 that produces circumferentially facing edges 200, 202 that allow a more positive grip to be created for engaging and turning of the housing part 114. A similar arrangement is provided at the opposite surface portion 196 and on the housing part 112.

In FIG. 27, the undercut 195' is shown modified with a longer vertical dimension, thereby producing longer gripping edges 200', 202'. This modified undercut arrangement may be used on any of the corresponding surface portions on the housing parts 112, 114.

With the above-described arrangement, the deodorant source and first and second housing parts are configured so that the first and second housing parts can be changed back and forth between the starting relationship and the assembled relationship by simply repositioning the housing parts 112, 114 without requiring the use of tools or separate fasteners.

As depicted, the change back and forth can be effected without requiring manual reconfiguration of any part of either of the housing parts.

Figure 34:
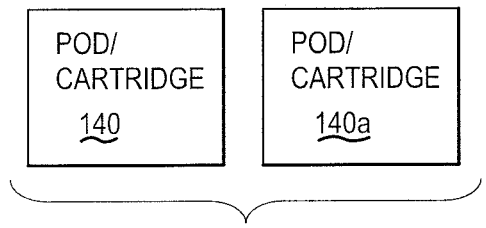
FIG. 34 is a schematic representation of interchangeable pods/cartridges, each made up of at least a housing and scent generator as shown in FIG. 10.

When the scent generator 126 has been exhausted, or when a scent generator capable of generating a different scent is desired, the active pod/cartridge 140 can be either filled with a new scent generator 126 or a new pod/cartridge 140*a*, as shown in FIG. 34, can be selected and used in place of the one that is removed.

To facilitate handling and bulk packaging of the pods/cartridges, a storage cup 206 may be utilized to accept the sealed or unsealed pod/cartridge. The cup 206 has a maintained shape with a cross-section tapering from top to bottom to facilitate guided introduction of the pod/cartridge. A cover 208 blocks and potentially seals a volume 210 occupied by the stored pod/cartridge.

Figure 35:
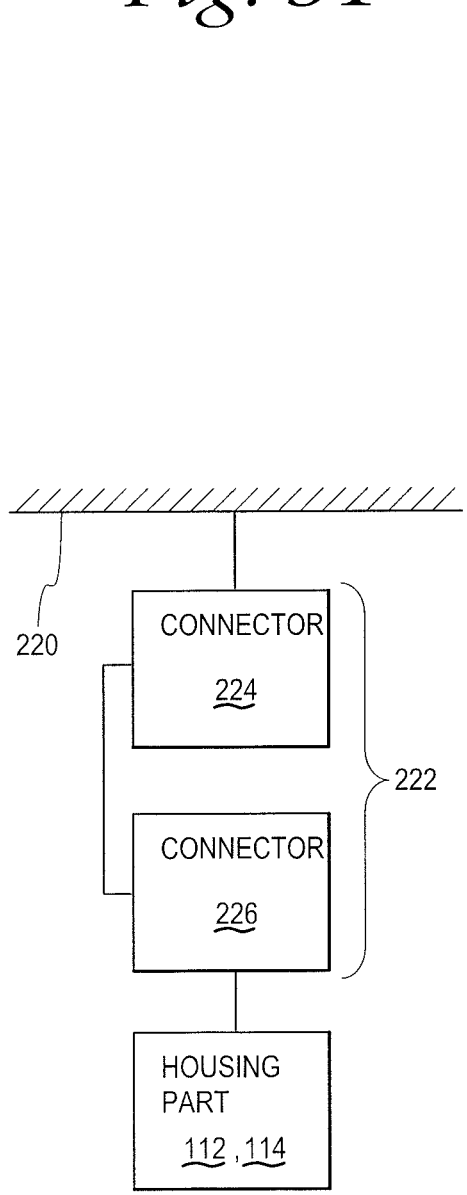
FIG. 35 is a schematic representation of one exemplary environment for the deodorizing apparatus, including showing one of the housing parts for supporting the deodorant source, being connected to a surface.

While the apparatus 110 can be conveniently placed on any surface without anchoring, mounting to a surface is also facilitated. For example, as shown in FIG. 35, one of the housing parts 112, 114 may be fixed to a surface 220, either permanently or releasably, by a connecting arrangement 222, depicted schematically in FIG. 35. A permanent connection might be established by a connecting arrangement that may, for example, involve use of a permanent adhesive. The depicted connecting arrangement 20 is made up of connectors 224, 226, one on the surface 220 and the other on the one of the housing parts 112, 114. For example, the connectors 224, 226 may use cooperating hook-and-loop surfaces that permit a releasable press fit connection. The connectors 224, 226 may form a bayonet-type connecting arrangement, a threaded connection, etc. No limitation is intended with respect to the connecting arrangement 222.

Figure 36:
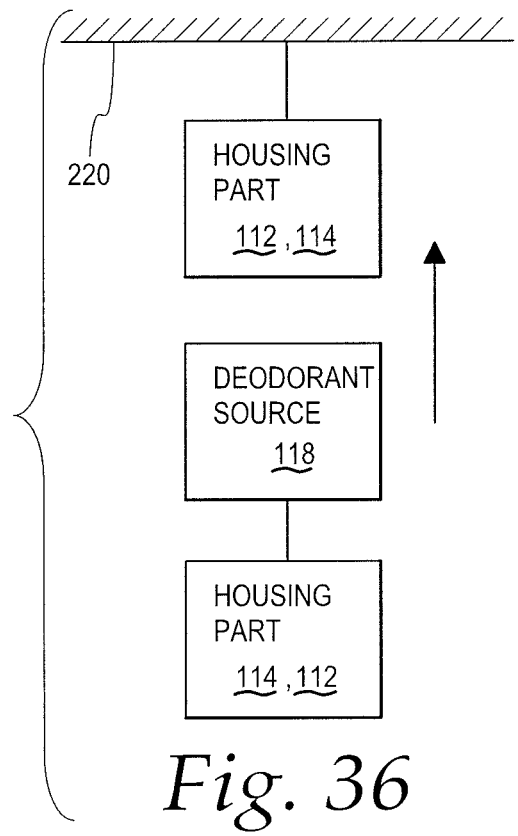
FIG. 36 is a view as in FIG. 35 wherein a cooperating housing part and deodorant source are being moved relative to the housing part, connected to the surface, to place the housing parts in the operative relationship and to support the deodorant source in an operative position.

Once the one housing part 112, 114 is fixed to the surface 220, the other housing part 112, 114 can be moved together with the deodorant source 118 up to the one housing part 112, 114, as shown in FIG. 36, to place the housing parts 112, 114 in the operative relationship and the deodorant source in the operative position.

In one preferred form, as described above, the housing parts 112, 114 may be changed between the operative and starting relationships by simply relatively moving them, potentially without changing a configuration of either housing part 112, 114 or the deodorant source—as by using magnetically attracting connectors, a bayonet arrangement, cooperating threads, etc.

Accordingly, with an exemplary environment being a locker room, a person can move efficiently from one locker to the next to place, remove, and replace scent generators.

In an exemplary environment, shown in FIGS. 35 and 36, the surface 220 might be a downwardly facing surface to which one of the housing parts 112, 114 is fixed. In a facility with multiple lockers, a user might change the pod/cartridge on a regular schedule which involves, in the case of using magnets for the connectors, a simple translation of one of the housing parts 112, 114 away from the fixed housing part 112, 114, removal of the existing pod/cartridge, substitution of a new pod/cartridge, and thereafter translation of the separated housing part 112, 114 towards the fixed housing part 112, 114.

Mounting on a downwardly facing surface of a locker may cause the apparatus to occupy generally unused space. Of course, the mounting surface may be any surface—such as one facing upwardly or horizontally.

Whether the connection relies on magnetism or another structure to maintain a relationship of the housing parts 112, 114, it is desirable in this particular application to allow changing of the relationship between the housing parts to be effected by simply relatively moving the housing parts 112, 114.

While various embodiments and aspects of the present invention have been described above, it should be understood that they have been presented by way of example only, and not limitation. Thus, the breadth and scope of the present invention should not be limited by any of the above exemplary embodiments.

This application—taken as a whole with the abstract, specification, and drawings being combined—provides sufficient information for a person having ordinary skill in the art to practice the invention as disclosed herein. Any measures necessary to practice this invention are well within the skill of a person having ordinary skill in this art after that person has made a careful study of this disclosure.

Because of this disclosure and solely because of this disclosure, modification of this device and method can become clear to a person having ordinary skill in this particular art. Such modifications are clearly covered by this disclosure.

The foregoing disclosure of specific embodiments is intended to be illustrative of the broad concepts comprehended by the invention.

The invention claimed is:

1. A portable deodorizing apparatus comprising:
   a housing comprising first and second releasably joinable parts; and
   a deodorant source,
   the first housing part having at least a first connector and the second housing part having at least a second connector,
   the at least first connector and the at least second connector configured to be: a) engaged so as to thereby maintain the first and second housing parts in an operative relationship as an incident of relatively moving the first and second housing parts from a starting relationship, separated from each other, into the operative relationship; and b) disengaged as an incident of relatively moving the first and second housing parts with the first and second housing parts in the operative relationship, so as to thereby allow the first and second housing parts to be changed from the operative relationship into the starting relationship,
   the first and second housing parts and deodorant source configured so that with the first and second housing parts in the operative relationship the deodorant source is maintained in an operative position wherein deodorant from the deodorant source is diffused into a space within which the deodorizing apparatus is placed,
   wherein the deodorant source and first and second housing parts are configured so that the first and second housing parts can be changed back and forth between: a) the starting relationship; and b) the assembled relationship without requiring manual reconfiguration of any part of either of the first and second housing parts.

2. The portable deodorizing apparatus according to claim 1 wherein the at least first connector and the at least second connector are magnetically attracted to each other, wherein as an incident of moving the first and second housing parts from the starting relationship into the operative relationship, a magnetic attraction force is generated between the at least first connector and the at least second connector tending to: a) urge the first and second housing parts towards the operative relationship; and b) maintain the operative relationship of the first and second housing parts.

3. The portable deodorizing apparatus according to claim 1 wherein with the first and second housing parts in the operative relationship and the deodorant source in the operative position, the deodorant source is captive between the first and second housing parts.

4. The portable deodorizing apparatus according to claim 1 wherein the deodorant source comprises a housing and a scent generator supported by the housing and the deodorant source housing and one of the first and second housing parts are configured so that the deodorant source housing is movable guidingly relative to the one of the first and second housing parts along an axis.

5. The portable deodorizing apparatus according to claim 4 wherein the first and second housing parts are relatively movable along the axis in changing between the starting relationship and the operative relationship.

6. The portable deodorizing apparatus according to claim 5 wherein the first and second housing parts have a same configuration.

7. The portable deodorizing apparatus according to claim 5 wherein the first and second housing parts each has a cup shape opening in an axial direction with the first and second housing parts in the operative relationship, the first housing part having a first edge extending around the axis and the second housing part having a second edge extending around the axis, with the first and second housing parts in the operative relationship the first and second edges are one of: a) abutted to each other; and b) adjacent to each other, the cup shapes on the first and second housing parts in the operative relationship cooperatively defining a receptacle for the deodorant source.

8. The portable deodorizing apparatus according to claim 7 wherein the at least first connector is at or adjacent to the first edge and the at least second connector is at or adjacent the second edge.

9. The portable deodorizing apparatus according to claim 4 wherein the deodorant source housing has a peripheral wall extending around the axis with the first and second housing parts in the operative relationship and the deodorant source in the operative position.

10. The portable deodorizing apparatus according to claim 9 wherein at least one of the first and second housing parts has a peripheral wall extending around the axis and through which a plurality of openings are formed and with the first and second housing parts in the operative relationship and the deodorant source in the operative position, scent from the scent generator diffuses through: a) at least one opening in the peripheral wall on the deodorant source housing; and b) the at least one opening formed through the peripheral wall on the at least one of the first and second housing parts and into a space in which the portable deodorizing apparatus is located.

11. The portable deodorizing apparatus according to claim 4 wherein the scent generator comprises an evaporative gel.

12. The portable deodorizing apparatus according to claim 4 wherein the deodorant source housing and first and second housing parts are configured so that the deodorant source housing is movable guidingly relative to each of the first and second housing parts around the axis.

13. The portable deodorizing apparatus according to claim 12 wherein with the first and second housing parts in the operative relationship and the deodorant source in the operative position, the first and second housing parts and deodorant source housing are relatively movable guidingly, each relative to the other, around a common axis.

14. The portable deodorizing apparatus according to claim 13 wherein the at least first connector and at least second connector are magnetically attracted to each other, with the first and second housing parts in the operative relationship and the deodorant source in the operative position, one of the first and second housing parts can be moved guidingly relative to the other of the first and second housing parts to thereby relatively move the at least first connector and the at least second connector so as to thereby reduce or eliminate a magnetic attraction force between the at least first connector and the at least second connector to thereby facilitate movement of the first and second housing parts into the starting relationship.

15. The portable deodorizing apparatus according to claim 14 wherein at least one of the first and second housing parts has a peripheral wall with radially oppositely facing, substantially flat surface portions that facilitate grasping by a user.

16. The portable deodorizing apparatus according to claim 15 wherein at least one of the radially oppositely facing surface portions has a circumferentially facing edge that facilitates gripping by a user.

17. The portable deodorizing apparatus according to claim 1 wherein each of the first and second housing parts has a cup shape and with the first and second housing parts in the operative relationship the cup shapes on the first and second housing parts open, each towards the other.

18. The portable deodorizing apparatus according to claim 1 wherein each of the first and second connectors is a magnet.

19. The portable deodorizing apparatus according to claim 1 wherein the deodorant source and first and second housing parts are configured so that the first and second housing parts can be changed back and forth between: a) the starting relationship; and b) the assembled relationship without requiring use of tools or separate fasteners.

20. The portable deodorizing apparatus according to claim 1 wherein the deodorant source is in the form of a first cartridge comprising a housing and a scent generator on the housing and further in combination with a second cartridge that is interchangeable with the first cartridge so that the second cartridge can be used: a) when the scent generator on the first cartridge is exhausted; and b) when it is desired to use a scent generator on the second cartridge that is different than the scent generator on the first cartridge.

21. A method of installing a portable deodorizing device in a space bounded by a wall surface, the method comprising the steps of:
 a) obtaining a portable deodorizing device comprising: a housing comprising first and second releasably joinable parts; and a deodorant source, the first housing part having at least a first connector and the second housing part having at least a second connector, the at least first connector and the at least second connector configured to be: a) engaged so as to thereby maintain the first and second housing parts in an operative relationship as an incident of relatively moving the first and second housing parts from a starting relationship, separated from each other, into the operative relationship; and b) disengaged as an incident of relatively moving the first and second housing parts with the first and second housing parts in the operative relationship, so as to thereby allow the first and second housing parts to be changed from the operative relationship into the starting relationship, the first and second housing parts and deodorant source configured so that with the first and second housing parts in the operative relationship the deodorant source is maintained in an operative position wherein deodorant from the deodorant source is diffused into a space within which the deodorizing apparatus is placed;
 b) fixing one of the first and second housing parts to the wall surface;
 c) with the one of the first and second housing parts fixed to the wall surface, repositioning the other of the housing parts and deodorant source relative to the one of the first and second housing parts to thereby place and maintain the first and second housing parts in the operative relationship and the deodorant source in the operative position; and
 d) with the one of the first and second housing parts remaining fixed to the wall surface and the first and second housing parts in the operative relationship and the deodorant source in the operative position, repositioning the other of the first and second housing parts relative to the one of the first and second housing parts while maintaining the one of the first and second housing parts fixed to the wall surface to disengage the first and second connectors and allow the other of the first and second housing parts to be separated from the one of the first and second housing parts.

22. The method of claim 21 wherein the step of repositioning the other of the first and second housing parts and deodorant source is performed without requiring use of tools or separate fasteners and without requiring changing of a configuration of any of the first and second housing parts and the deodorant source.

23. The method of claim 21 wherein the wall surface faces in a downward direction.

24. A portable deodorizing apparatus comprising:
 a housing comprising first and second releasably joinable parts; and
 a deodorant source,
 the first housing part having at least a first connector and the second housing part having at least a second connector,
 the at least first connector and the at least second connector configured to be: a) engaged so as to thereby maintain the first and second housing parts in an operative relationship as an incident of relatively moving the first and second housing parts from a starting relationship, separated from each other, into the operative relationship; and b) disengaged as an incident of relatively moving the first and second housing parts with the first and second housing parts in the operative relationship, so as to thereby allow the first and second housing parts to be changed from the operative relationship into the starting relationship,
 the first and second housing parts and deodorant source configured so that with the first and second housing parts in the operative relationship the deodorant source is maintained in an operative position wherein deodorant from the deodorant source is diffused into a space within which the deodorizing apparatus is placed,
wherein the at least first connector and the at least second connector are magnetically attracted to each other, wherein as an incident of moving the first and second housing parts from the starting relationship into the operative relationship, a magnetic attraction force is generated between the at least first connector and the at least second connector tending to: a) urge the first and second housing parts towards the operative relationship; and b) maintain the operative relationship of the first and second housing parts,
wherein the at least first connector comprises the first connector and a third connector on the first housing part and the at least second connector comprises the second connector and a fourth connector on the second housing part,
wherein the third connector and the fourth connector are magnetically attracted to each other, wherein as an incident of moving the first and second housing parts from the starting relationship into the operative relationship, a magnetic attraction force is generated between the third connector and the fourth connector tending to: a) urge the first and second housing parts towards the operative relationship, and to maintain the operative relationship of the first and second housing parts.

25. A portable deodorizing apparatus comprising:
a housing comprising first and second releasably joinable parts; and
a deodorant source,
the first housing part having at least a first connector and the second housing part having at least a second connector,
the at least first connector and the at least second connector configured to be: a) engaged so as to thereby maintain the first and second housing parts in an operative relationship as an incident of relatively moving the first and second housing parts from a starting relationship, separated from each other, into the operative relationship; and b) disengaged as an incident of relatively moving the first and second housing parts with the first and second housing parts in the operative relationship, so as to thereby allow the first and second housing parts to be changed from the operative relationship into the starting relationship,
the first and second housing parts and deodorant source configured so that with the first and second housing parts in the operative relationship the deodorant source is maintained in an operative position wherein deodorant from the deodorant source is diffused into a space within which the deodorizing apparatus is placed,
wherein the deodorant source comprises a housing and a scent generator supported by the housing and the deodorant source housing and one of the first and second housing parts are configured so that the deodorant source housing is movable guidingly relative to the one of the first and second housing parts along an axis.

26. A portable deodorizing apparatus comprising:
a housing comprising first and second releasably joinable parts; and
a deodorant source,
the first housing part having at least a first connector and the second housing part having at least a second connector,
the at least first connector and the at least second connector configured to be: a) engaged so as to thereby maintain the first and second housing parts in an operative relationship as an incident of relatively moving the first and second housing parts from a starting relationship, separated from each other, into the operative relationship; and b) disengaged as an incident of relatively moving the first and second housing parts with the first and second housing parts in the operative relationship, so as to thereby allow the first and second housing parts to be changed from the operative relationship into the starting relationship,
the first and second housing parts and deodorant source configured so that with the first and second housing parts in the operative relationship the deodorant source is maintained in an operative position wherein deodorant from the deodorant source is diffused into a space within which the deodorizing apparatus is placed,
wherein the deodorant source comprises a housing and a scent generator supported by the housing and the deodorant source housing and one of the first and second housing parts are configured so that the deodorant source housing is movable guidingly relative to the one of the first and second housing parts along an axis,
wherein the first and second housing parts are relatively movable along the axis in changing between the starting relationship and the operative relationship,
wherein the first and second housing parts have a same configuration.

27. A portable deodorizing apparatus comprising:
a housing comprising first and second releasably joinable parts; and
a deodorant source,
the first housing part having at least a first connector and the second housing part having at least a second connector,
the at least first connector and the at least second connector configured to be: a) engaged so as to thereby maintain the first and second housing parts in an operative relationship as an incident of relatively moving the first and second housing parts from a starting relationship, separated from each other, into the operative relationship; and b) disengaged as an incident of relatively moving the first and second housing parts with the first and second housing parts in the operative relationship, so as to thereby allow the first and second housing parts to be changed from the operative relationship into the starting relationship,
the first and second housing parts and deodorant source configured so that with the first and second housing parts in the operative relationship the deodorant source is maintained in an operative position wherein deodorant from the deodorant source is diffused into a space within which the deodorizing apparatus is placed,
wherein the deodorant source comprises a housing and a scent generator supported by the housing and the deodorant source housing and one of the first and second housing parts are configured so that the deodorant source housing is movable guidingly relative to the one of the first and second housing parts along an axis,
wherein the deodorant source housing has a peripheral wall extending around the axis with the first and second housing parts in the operative relationship and the deodorant source in the operative position,
wherein at least one of the first and second housing parts has a peripheral wall extending around the axis and through which a plurality of openings are formed and with the first and second housing parts in the operative relationship and the deodorant source in the operative position, scent from the scent generator diffuses through: a) at least one opening in the peripheral wall on the deodorant source housing; and b) the at least one opening formed through the peripheral wall on the at least one of the first and second housing parts and into a space in which the portable deodorizing apparatus is located.

28. A portable deodorizing apparatus comprising:

a housing comprising first and second releasably joinable parts; and a deodorant source, the first housing part having at least a first connector and the second housing part having at least a second connector, the at least first connector and the at least second connector configured to be: a) engaged so as to thereby maintain the first and second housing parts in an operative relationship as an incident of relatively moving the first and second housing parts from a starting relationship, separated from each other, into the operative relationship; and b) disengaged as an incident of relatively moving the first and second housing parts with the first and second housing parts in the operative relationship, so as to thereby allow the first and second housing parts to be changed from the operative relationship into the starting relationship, the first and second housing parts and deodorant source configured so that with the first and second housing parts in the operative relationship the deodorant source is maintained in an operative position wherein deodorant from the deodorant source is diffused into a space within which the deodorizing apparatus is placed, wherein the deodorant source comprises a housing and a scent generator supported by the housing and the deodorant source housing and one of the first and second housing parts are configured so that the deodorant source housing is movable guidingly relative to the one of the first and second housing parts along an axis, wherein the deodorant source housing and first and second housing parts are configured so that the deodorant source housing is movable guidingly relative to each of the first and second housing parts around the axis, wherein with the first and second housing parts in the operative relationship and the deodorant source in the operative position, the first and second housing parts and deodorant source housing are relatively movable guidingly, each relative to the other, around a common axis, wherein the at least first connector and at least second connector are magnetically attracted to each other, with the first and second housing parts in the operative relationship and the deodorant source in the operative position, one of the first and second housing parts can be moved guidingly relative to the other of the first and second housing parts to thereby relatively move the at least first connector and the at least second connector so as to thereby reduce or eliminate a magnetic attraction force between the at least first connector and the at least second connector to thereby facilitate movement of the first and second housing parts into the starting relationship.

* * * * *